US00PP29104P2

(12) United States Plant Patent
Bruin

(10) Patent No.: US PP29,104 P2
(45) Date of Patent: Mar. 13, 2018

(54) ***HIBISCUS* PLANT NAMED 'AARTICUS'**

(50) Latin Name: *Hibiscus syriacus*
Varietal Denomination: Aarticus

(71) Applicant: Steven Joseph Bruin, Grand Rapids, MI (US)

(72) Inventor: Steven Joseph Bruin, Grand Rapids, MI (US)

( * ) Notice: Subject to any disclaimer, the term of this patent is extended or adjusted under 35 U.S.C. 154(b) by 0 days.

(21) Appl. No.: 14/999,595

(22) Filed: May 31, 2016

(51) Int. Cl.
*A01H 5/00* (2006.01)

(52) U.S. Cl.
USPC ..... Plt./257

(58) Field of Classification Search
USPC ..... Plt./257
CPC ..... A01H 5/02; A01H 5/00
See application file for complete search history.

(56) References Cited

PUBLICATIONS

New Plants and Flowers New variegatd *Hibiscus* Aug. 27, 2015, retrieved from the Internet at Jul. 24, 2017, retrieved from the <Internet at http://www.newplantsandflowers.com/new-variegated-hibiscus/> 1 p.*

Nursery Management New Varieties Jan. 18, 2016 retrieved on Jul. 18, 2017, retrieved from the Internet at <http://www.nurserymag.com/article/new-varieties-january-2016/> pp. 1, 8-9, 18-19.*

* cited by examiner

*Primary Examiner* — June Hwu
(74) *Attorney, Agent, or Firm* — Penny J. Aguirre

(57) ABSTRACT

A new cultivar of *Hibiscus* named 'Aarticus' that is characterized by its variegated foliage with green and creamy white to gold, its double flowers that open lavender in color and ages to violet blue, and its compact and rounded plant habit; reaching 0.9 to 1.2 m in height and spread.

2 Drawing Sheets

Botanical classification: *Hibiscus syriacus.*
Cultivar designation: 'Aarticus'.

BACKGROUND OF THE INVENTION

The present invention relates to a new and distinct cultivar of *Hibiscus* plant of hybrid origin, botanically known as *Hibiscus syriacus* 'Aarticus' and will be referred to hereafter by its cultivar name, 'Aarticus'. 'Aarticus' is a new cultivar of *Hibiscus* grown for use as a landscape and container plant.

The Inventor discovered the new cultivar in spring of 2003 as a naturally occurring branch mutation of *Hibiscus syriacus* 'Ardens' (not patented) that was growing in a container outdoors in a production block at a nursery in Grand Rapids, Mich.

Asexual propagation of the new cultivar was first accomplished by stem cuttings in Grand Rapids, Mich. in July of 2004 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Aarticus'. These attributes in combination distinguish 'Aarticus' as a new and distinct cultivar of *Hibiscus.*

1. 'Aarticus' exhibits variegated foliage with green and creamy white to gold.
2. 'Aarticus' exhibits double flowers that open lavender in color and ages to violet blue.

3. 'Aarticus' exhibits a compact and rounded plant habit; reaching 0.9 to 1.2 m in height and spread.

The parent plant of 'Aarticus', 'Ardens', differs from 'Aarticus' in having non-variegated foliage, in having a more vigorous growth habit, and in having an upright and larger plant habit. 'Aarticus' can also be most closely compared to the cultivars 'America Irene Scott' (U.S. Plant Pat. No. 20,579) and 'Notwoodone' (U.S. Plant Pat. No. 12,619). 'America Irene Scott' is similar to 'Aarticus' in having variegated foliage. 'America Irene Scott' differs from 'Aarticus' in having foliage that is less variegated, in having flowers that are pink in color, and in having a larger and more vase-shaped plant habit. 'Notwoodone' is similar to 'Aarticus' in having double flowers that are lavender in color. 'Notwoodone' differs from 'Aarticus' in having foliage that is non-variegated and in having a larger and more upright plant habit.

BRIEF DESCRIPTION OF THE DRAWINGS

The accompanying colored photograph illustrates the overall appearance and distinct characteristics of the new *Hibiscus.*

The photograph in FIG. 1 was taken a six year-old plant of 'Aarticus' as grown in a trial garden in Grand Rapids, Mich. and provides a view of the plant habit of 'Aarticus'.

Figure 1:
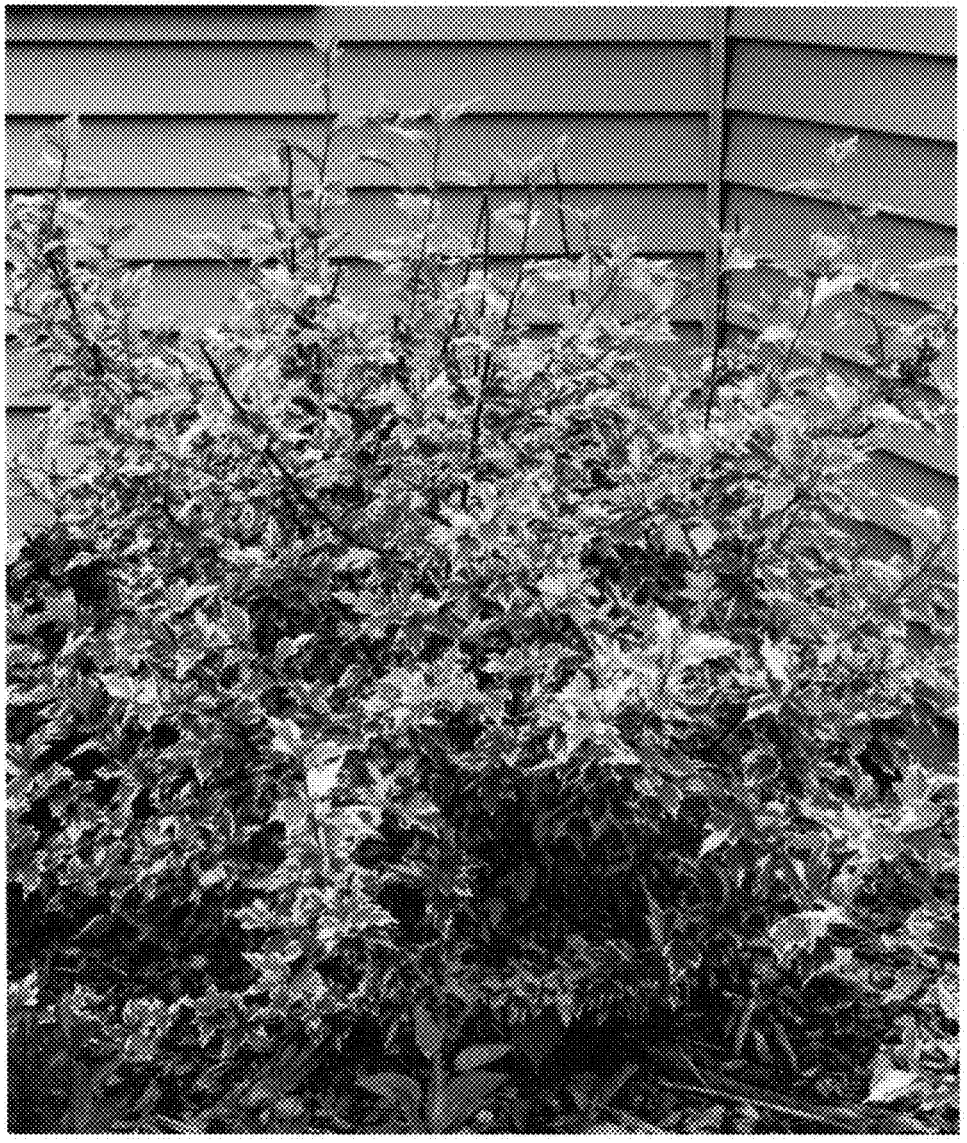
Figure 2:
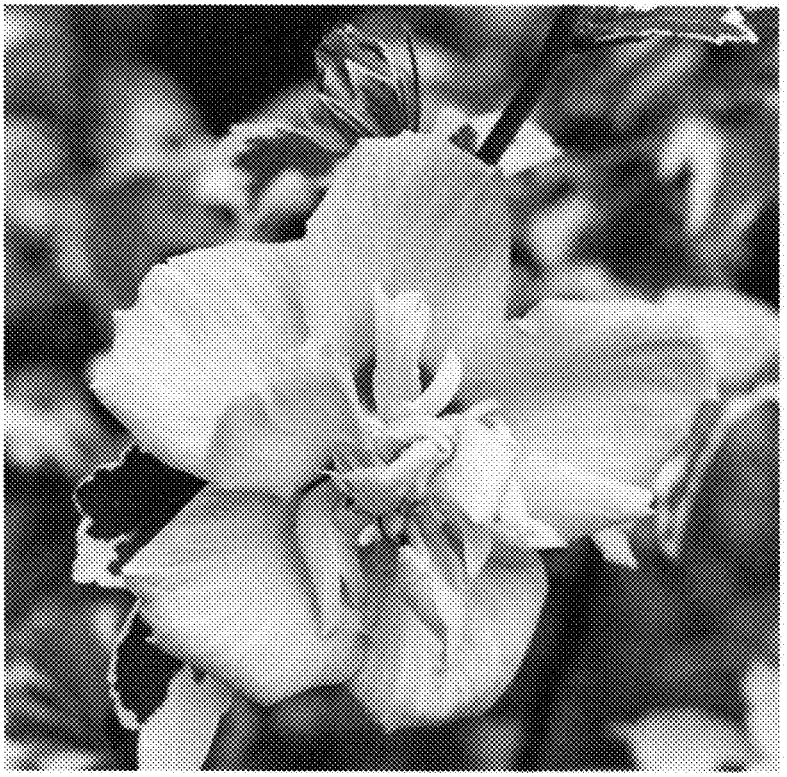
Figure 3:
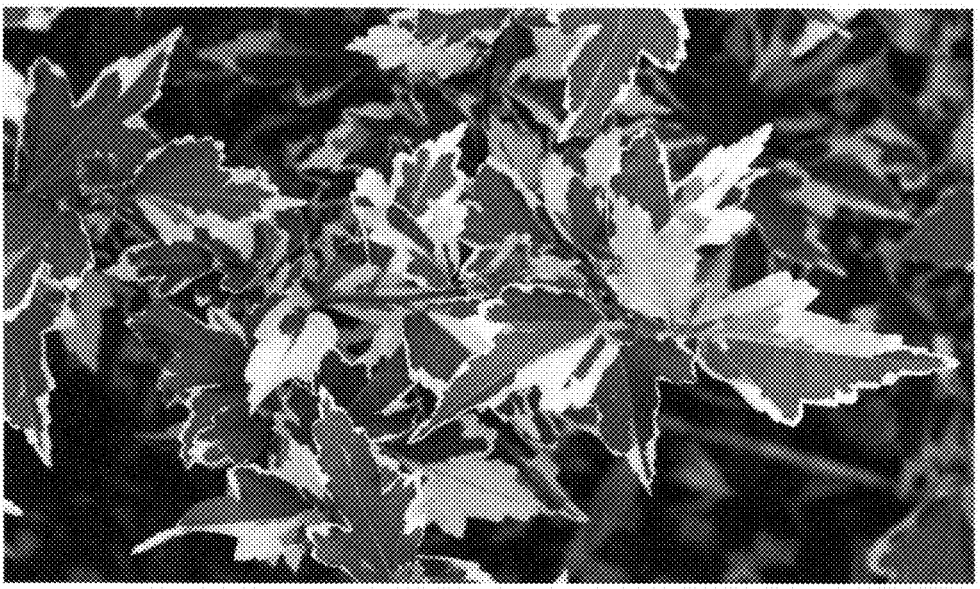

The photographs in FIG. 2 and FIG. 3 were taken a four year-old plant of 'Aarticus' as grown in a trial garden in Cottage Grove, Minn.

The photograph in FIG. 2 provides a close-up view of a flower of 'Aarticus'.

The photograph in FIG. 3 provides a close-up view of the foliage of 'Aarticus'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 2 year-old plants of the new cultivar as grown in one-gallon containers in a greenhouse in St. Paul, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—Mid to late summer in Grand Rapids, Mich.

*Plant type.*—Deciduous shrub.

*Plant habit.*—Compact and round.

*Height and spread.*—Reaches 50 cm in height and 35 cm in spread as a two year-old plant and 0.9 m to 1.2 m in height and spread in the landscape.

*Hardiness.*—At least in U.S.D.A. Zones 5 to 9.

*Diseases.*—Not susceptible or resistance to diseases has been observed to date.

*Root description.*—Fibrous roots, a blend of 162A and 158A in color.

*Root development.*—Roots initiate in 14 to 20 days and fully develop in a plug in 43 to 50 days.

*Propagation.*—Stem cuttings.

*Growth rate.*—Moderate.

Stem description:

*Shape.*—Rounded.

*Stem color.*—New growth; 140A, maturing wood; 197B, mature wood; a blend of N187A and 200B.

*Stem size.*—Main stems; an average of 16 cm in length and 1.3 cm in width, lateral stems; an average of 23 cm in length and 5 mm in diameter.

*Stem surface.*—New growth; smooth and dull, maturing wood; finely striated, mature wood; striated.

*Stem aspect.*—Held upright to an average angle of 45° (0°=vertical).

*Stem strength.*—Strong.

*Branching.*—Self-branching, an average of 1 main stem and 5 lateral branches per main stem in a one-gallon container.

*Internode.*—Average of 2 cm.

Foliage description:

*Leaf shape.*—Ovate, irregularly 3 lobed.

*Leaf division.*—Simple.

*Leaf base.*—Cordate to obtuse.

*Leaf apex.*—Acute.

*Leaf venation.*—Pinnate, 195A on upper surface and lower surface matches leaf color.

*Leaf margins.*—Lobes of shallow to moderate depth, lobe margins irregularly crenate and serrate.

*Leaf attachment.*—Petiolate.

*Leaf arrangement.*—Alternate.

*Leaf orientation.*—Held downward to horizontal.

*Leaf aspect.*—Slightly cupped downward to flat.

*Leaf surface.*—Upper and lower surface dull.

*Leaf color.*—Young and mature leaves upper surfaces; variegated with NN137A, 194A, 155B, and 160C, young and mature lower surfaces; variegated with NN137A, 160A, 155B, 191A and 194A. The variegation pattern is variable; typically the cream white (155B) is located narrowly on the leaf margins, with some leaves that are primarily creamy white (155B) or gold (160B) and up to ¾ that are creamy white (155B) with grey-green (191A and 194A) and green (NN137A).

*Leaf size.*—Average of 5 cm in length, and 3.5 cm in width.

*Leaf quantity.*—Average of 28 leaves per lateral branch 22 cm in length, up to 3 leaves in one cluster.

*Petioles.*—Average of 1 cm in length and 1 mm in diameter, 144A in color, finely pubescent surface.

Flower description:

*Inflorescence type.*—Double flowers are solitary or in clusters of 3 at terminus and occasional solitary flowers on upper nodes.

*Inflorescence size.*—With one flower open and 2 buds an average of 6 cm in width and 4 cm in height.

*Lastingness of flowers.*—About 4 days, self cleaning.

*Flower size.*—An average of 4 cm in depth and 7 cm in diameter.

*Flower fragrance.*—Very faint.

*Flower shape.*—Rotate, carnation-like.

*Flower number.*—3 to 5 per lateral stem.

*Flower aspect.*—Upright to outward.

*Flower bud.*—Elliptic-globose in shape, an average of 1.5 cm in length and 1.2 cm in width, 144D in color with apex (petal portion) 79C, surface pubescent.

*Flower attachment.*—Peduncle.

*Petal and petaloid number.*—Average of 14 petals and 26 petaloids (some with rudimentary stamens attached).

*Petal and petaloid shape.*—Petals; orbicular to broadly oblanceolate to elliptic, petaloids; primarily oblanceolate with some twisted and distorted, outermost petal attitude is horizontal.

*Petal and petaloid color.*—Upper and lower surface when newly opening; a blend of 76A and 76B with veins 76C, upper and lower surface when mature; a blend of 85A and 91A, upper and lower surface fading before drop; a blend of 91A and 94B, basal spot (not highly visible) at all stages on both surfaces; 59B with the very base NN155C, smaller inner petaloids lack a basal spot.

*Petal and petaloid surface.*—Both surfaces smooth and dull with petal spot on petals satiny.

*Petal and petaloid margins.*—Entire to very slightly undulate.

*Petal and petaloid apex.*—Petals rounded to acute, petaloids acute.

*Petal and petaloid base.*—Petals cuneate, petaloids attenuate.

*Petal and petaloid size.*—Petals; up to 3.4 cm in length and 2.4 cm in width, petaloids; range from 7 mm in length and 3 mm in width to 2.5 cm in length and 7 mm in width, petal eye zone small.

*Sepal number.*—5.

*Sepal shape.*—Elliptic.

*Sepal margin.*—Entire.

*Sepal size.*—Average of 1.5 cm in length and 6 mm in width (free potion is triangular in shape and 6 mm in length and width.

*Sepal aspect.*—Upright and spreading.

*Sepal surface.*—Outer surface puberulent, inner surface glabrous and glossy.

*Sepal apex.*—Acute.

*Sepal base.*—Fused, lower ⅔.

*Sepal color.*—Young and mature outer and inner surface; a blend of 145C, 138A, and 138B.

*Calyx.*—Campanulate in shape, average of 1 cm in depth and 2.3 cm in diameter.

*Peduncles.*—An average of 3 cm in length and 2 mm in diameter, strong and stout, held upright to outward from stem, 138B in color, pubescent surface.

*Pedicels.*—Not present, flowers emerge from terminal leaf axils.

*Bracts.*—7 to 9 bracts held close to calyx, linear to narrowly oblanceolate in shape, apiculate apex, truncate base, average of 1 cm in length and 1 mm in width, a color 145C with occasional vertical lines of 138C on inner and outer surface, surface is slightly pubescent on inner and outer surface.

Reproductive organs:

*Gynoecium.*—1 pistil, stigmas; 5, club-shaped, 157D in color, and 1.5 mm in diameter, style arms; NN155B in color and 2 mm in length, style; 1 cm in length and 1.5 mm in width, glabrous and NN155B in color, ovary; urn to globose in shape, 5 mm in length and width, glandular surface, 4D in color.

*Androecium.*—Stamens; not intact, all have become petaloids, only rudimentary and distorted ones occurring on some of the petaloids, about 1 mm in length and 162B in color, pollen; none observed.

*Fruit/seeds.*—None observed to date.

It is claimed:

1. A new and distinct cultivar of *Hibiscus* plant named 'Aarticus' as herein illustrated and described.

* * * * *